United States Patent
Harari

(10) Patent No.: US 10,390,924 B2
(45) Date of Patent: *Aug. 27, 2019

(54) SYSTEM AND METHOD FOR PELVIC FLOOR REPAIR

(71) Applicant: POP MEDICAL SOLUTIONS LTD., Tel Aviv (IL)

(72) Inventor: Boaz Harari, Ganei-Tikva (IL)

(73) Assignee: POP MEDICAL SOLUTIONS LTD., Tel-Aviv (IL)

(*) Notice: Subject to any disclaimer, the term of this patent is extended or adjusted under 35 U.S.C. 154(b) by 17 days.

This patent is subject to a terminal disclaimer.

(21) Appl. No.: 15/651,472

(22) Filed: Jul. 17, 2017

(65) Prior Publication Data

US 2017/0348085 A1     Dec. 7, 2017

Related U.S. Application Data

(63) Continuation of application No. 15/342,144, filed on Nov. 3, 2016, now Pat. No. 9,737,391, which is a (Continued)

(51) Int. Cl.
*A61F 2/00* (2006.01)
*A61B 8/12* (2006.01)
(Continued)

(52) U.S. Cl.
CPC .......... *A61F 2/0063* (2013.01); *A61B 8/0841* (2013.01); *A61B 8/12* (2013.01);
(Continued)

(58) Field of Classification Search
CPC ............ A61B 17/42; A61B 2017/4216; A61B 2017/4241; A61B 17/0401; A61B 2017/0409; A61B 2017/0411
(Continued)

(56) References Cited

U.S. PATENT DOCUMENTS

| 4,877,033 A | 10/1989 | Seitz, Jr. |
|---|---|---|
| 5,220,690 A | 6/1993 | Hoos |

(Continued)

FOREIGN PATENT DOCUMENTS

| CA | 2093824 | 10/1994 |
|---|---|---|
| DE | 2910410 | 12/1979 |

(Continued)

OTHER PUBLICATIONS

An Office Action dated Nov. 15, 2017, which issued during the prosecution of U.S. Appl. No. 14/667,954.
(Continued)

*Primary Examiner* — John P Lacyk
(74) *Attorney, Agent, or Firm* — Sughrue Mion, PLLC

(57) ABSTRACT

A method of repairing a pelvic floor disorder and a system for carrying out the method are provided. The method is effected by positioning an imaging device in an abdominal, rectal, perianal or vaginal cavity, advancing a surgical instrument through a vaginal wall under guidance of the imaging device to thereby reach a target tissue and using the surgical instrument to attach the tissue repair device to the target tissue.

3 Claims, 14 Drawing Sheets

Related U.S. Application Data continuation of application No. 14/366,002, filed as application No. PCT/IL2012/050548 on Dec. 20, 2012, now Pat. No. 9,517,058.

(60) Provisional application No. 61/578,261, filed on Dec. 21, 2011.

(51) Int. Cl.

| | | |
|---|---|---|
| *A61B 17/42* | (2006.01) | |
| *A61B 17/00* | (2006.01) | |
| *A61B 8/08* | (2006.01) | |
| *A61B 17/04* | (2006.01) | |
| *A61B 17/34* | (2006.01) | |
| *A61B 8/00* | (2006.01) | |
| *A61B 90/00* | (2016.01) | |

(52) U.S. Cl.
CPC .... *A61B 17/00234* (2013.01); *A61B 17/0401* (2013.01); *A61B 17/0469* (2013.01); *A61B 17/42* (2013.01); *A61F 2/0045* (2013.01); *A61B 8/445* (2013.01); *A61B 2017/00296* (2013.01); *A61B 2017/0409* (2013.01); *A61B 2017/0464* (2013.01); *A61B 2017/3413* (2013.01); *A61B 2017/3452* (2013.01); *A61B 2090/3925* (2016.02); *A61F 2002/0072* (2013.01)

(58) Field of Classification Search
USPC .......................................................... 600/37
See application file for complete search history.

(56) References Cited

U.S. PATENT DOCUMENTS

| | | | |
|---|---|---|---|
| 6,066,104 A | 5/2000 | Dao et al. | |
| 6,332,888 B1 | 12/2001 | Levy et al. | |
| 6,355,017 B2 | 3/2002 | Buttgen et al. | |
| 6,506,190 B1 | 1/2003 | Walshe | |
| 6,602,251 B2 | 8/2003 | Burbank et al. | |
| 7,393,319 B2 | 7/2008 | Merade et al. | |
| 8,257,366 B2 | 9/2012 | Schneider et al. | |
| 8,535,216 B2 | 9/2013 | Chu et al. | |
| 8,617,183 B2 | 12/2013 | Schneider et al. | |
| 9,451,944 B2 | 9/2016 | Schneider et al. | |
| 9,517,058 B2 * | 12/2016 | Harari ................. | A61B 8/12 |
| 9,737,391 B2 * | 8/2017 | Harari ................. | A61B 8/12 |
| 2001/0041914 A1 | 11/2001 | Frazier et al. | |
| 2005/0234305 A1 | 10/2005 | Licciardi | |
| 2005/0250987 A1* | 11/2005 | Ewers ................. | A61B 1/0014 |
| | | | 600/102 |
| 2006/0047285 A1 | 3/2006 | Fields | |
| 2008/0064962 A1 | 3/2008 | Oonuki et al. | |
| 2008/0171940 A1 | 7/2008 | McGahan | |
| 2008/0207988 A1 | 8/2008 | Hanes | |
| 2008/0208216 A1 | 8/2008 | Cerier | |
| 2009/0012557 A1 | 1/2009 | Osypka | |
| 2009/0216075 A1 | 8/2009 | Bell et al. | |
| 2010/0274074 A1 | 10/2010 | Khamis et al. | |
| 2011/0092985 A1 | 4/2011 | Gaynor et al. | |
| 2011/0092991 A1 | 4/2011 | Gaynor et al. | |
| 2011/0196389 A1 | 8/2011 | Schneider et al. | |
| 2012/0123410 A1 | 5/2012 | Craig | |
| 2014/0100580 A1 | 4/2014 | Yu et al. | |
| 2014/0324072 A1 | 10/2014 | Harari et al. | |
| 2015/0005586 A1 | 1/2015 | Williams | |
| 2015/0320442 A1* | 11/2015 | Harari ................ | A61B 17/0482 |
| | | | 606/119 |
| 2016/0235461 A1 | 8/2016 | Sumko | |
| 2017/0049548 A1 | 2/2017 | Harari et al. | |
| 2017/0196671 A1 | 7/2017 | Harari et al. | |

FOREIGN PATENT DOCUMENTS

| | | |
|---|---|---|
| DE | 10321012 | 12/2004 |
| JP | 2004-509685 A | 4/2004 |
| JP | 2008-510589 A | 4/2008 |
| JP | 2008-523926 A | 7/2008 |
| WO | 95/14438 | 6/1995 |
| WO | 2011/082350 | 7/2011 |
| WO | 2012/047626 | 4/2012 |
| WO | 2013/093924 | 6/2013 |
| WO | 2015/189843 | 12/2015 |

OTHER PUBLICATIONS

An English translation of an Office Action dated Oct. 10, 2017 which issued during the prosecution of Japanese Patent Application No. 2016-572283.
European Search Report dated Dec. 11, 2017 which issued during the prosecution of Applicant's European App No. 15806208.3.
An International Search Report and a Written Opinion both dated Mar. 17, 2017, which issued during the prosecution of Applicant's PCT/IL2016/051338.
An International Search Report and a Written Opinion both dated Nov. 2, 2015, which issued during the prosecution of Applicant's PCT/IL2015/050585.
An International Preliminary Report on Patentability dated Dec. 15, 2016, which issued during the prosecution of Applicant's PCT/IL2015/050585.
An International Search Report and a Written Opinion both dated May 9, 2013, which issued during the prosecution of Applicant's PCT/IL2012/050548.
An International Preliminary Report on Patentability dated Oct. 21, 2014, which issued during the prosecution of Applicant's PCT/IL2012/050548.
Rofaeel, A., M.D., Peng, Philip,M.B.B.S., F.R.C.P.C., Louis, I., M.D., & Chan, Vincent, M.D., F.R.C.P.C. (2008). Feasibility of real-time ultrasound for pudendal nerve block in patients with chronic perineal pain. Regional Anesthesia and Pain Medicine, 33(2), 139-45.
An Office Action dated Apr. 8, 2016, which issued during the prosecution of U.S. Appl. No. 14/366,002.
An Office Action dated Nov. 5, 2015, which issued during the prosecution of U.S. Appl. No. 14/366,002.
Notice of Allowance dated Aug. 12, 2016, which issued during the prosecution of U.S. Appl. No. 14/366,002.
Notice of Allowance dated May 12, 2017, which issued during the prosecution of U.S. Appl. No. 15/342,144.
An Office Action dated Jan. 17, 2017, which issued during the prosecution of U.S. Appl. No. 15/342,144.
U.S. Appl. No. 61/578,261, filed Dec. 21, 2011.
Office Action dated Jun. 22, 2017, which issued during the prosecution of U.S. Appl. No. 14/667,954.
Notice of Allowance dated Jun. 19, 2018, which issued during the prosecution of U.S. Appl. No. 14/667,954.

* cited by examiner

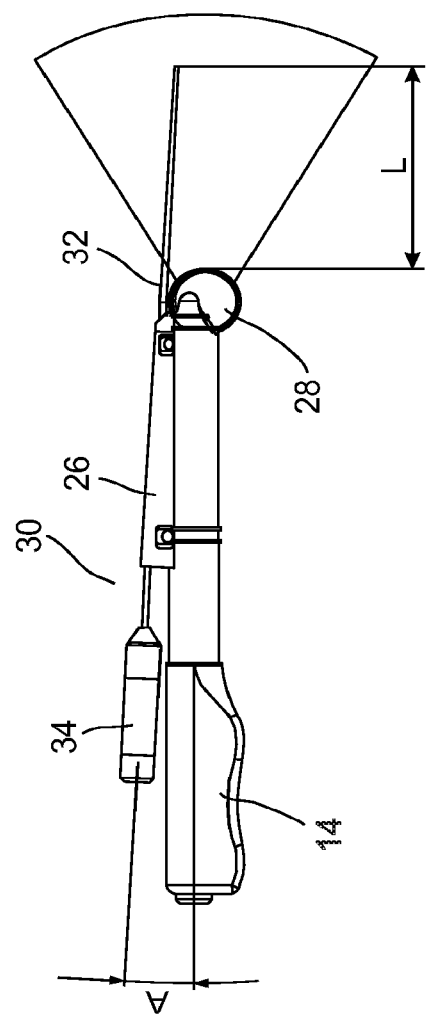

SYSTEM AND METHOD FOR PELVIC FLOOR REPAIR

RELATED APPLICATIONS

The present application is a continuation application of U.S. patent application Ser. No. 15/342,144 filed on Nov. 3, 2016, entitled SYSTEM AND METHOD FOR PELVIC FLOOR REPAIR, which is a continuation of U.S. patent application Ser. No. 14/366,002 filed on Jun. 17, 2014, now U.S. Pat. No. 9,517,058, which is a National Phase of PCT Patent Application No. PCT/IL2012/050548 having International Filing Date of Dec. 20, 2012, which claims the benefit of priority under 35 USC § 119(e) of U.S. Provisional Patent Application No. 61/578,261 filed on Dec. 21, 2011. The contents of the above applications are all incorporated by reference as if fully set forth herein in their entirety.

FIELD AND BACKGROUND OF THE INVENTION

The present invention relates to a system and method for rapid, safe and accurate access to pelvic floor tissues with minimal tissue trauma. Embodiments of the present invention relate to a system capable of guiding the positioning of a tissue repair device and/or implant in treatment of pelvic organ prolapse and pelvic floor herniation and/or relaxation.

Trans-vaginal pelvic floor repair is a surgical procedure which utilizes blunt tissue dissection to provide access to the sacrospinous ligament from the posterior vaginal wall. A sling or mesh is then anchored to the sacrospinous ligament and the vaginal apex or the uterine isthmical fibrotic ring, cervix or body, to thereby support prolapsing tissues and/or organs.

Although pelvic floor repair is a common procedure, access to the sacrospinous ligament is typically effected by improvised manual blunt dissection techniques and/or use of off the shelf instruments.

Centro-apical reconstruction is key for proper pelvic organ prolapse (POP) repair. The premium supportive pelvic structure is the sacro-spinous ligament (SSL) which is positioned at the posterior aspect of the pelvis. The SSL is a robust ligament and thus provides a long lasting solution. Since it is positioned high in the pelvis and medially the SSL provides a level 1 support (DeLancey) and reduces the likelihood of dyspareunia when utilized for prolapse repair.

Vaginal wall access to the SSL can be difficult and hazardous since organs and tissues surrounding the access path can easily be injured during dissection. Present day approach for accessing the SSL starts with an incision at the mid-line of the posterior or anterior vaginal wall followed by lateral dissection under the sub-mucosal fascia to the pelvic side wall and dissection towards the ischial spine to the mid SSL (MSSL).

This approach decreases risk of tissue injury by bypassing the bladder/rectum while maintaining accurate navigation along the above mentioned landmarks. Such an approach requires a high degree of skill and as such can lead to a high rate of complications; this prompted the FDA to issue a significant risk warning associated with POP reconstruction.

While reducing the present invention to practice, the present inventors have devised a system and method which can be used to directly access anatomical landmarks and structures such as the ischial spine and the sacro-spinous ligament from the vaginal cavity as well as guide a tissue repair device and fixate it to such anatomical landmarks with minimal associated tissue trauma.

SUMMARY OF THE INVENTION

According to one aspect of the present invention there is provided a method of repairing a pelvic floor disorder comprising: (a) positioning an imaging device in or against an abdominal, rectal, perianal or vaginal cavity; and (b) advancing a surgical instrument through a vaginal wall under guidance of the imaging device to thereby reach a target tissue; and (c) using the surgical instrument to attach the tissue repair device to the target tissue.

According to further features in preferred embodiments of the invention described below, the imaging device and the surgical instrument are attached via a housing.

According to still further features in the described preferred embodiments the housing includes a guide element for guiding a path of the surgical instrument through a vaginal wall.

According to still further features in the described preferred embodiments the imaging device is an ultrasound transducer and the guide element aligns the path of the surgical instrument with an imaging plane of the ultrasound transducer.

According to still further features in the described preferred embodiments the target tissue is a sacrospinous ligament.

According to still further features in the described preferred embodiments the vaginal wall is a posterior and/or lateral vaginal wall.

According to still further features in the described preferred embodiments the pelvic floor disorder is central pelvic apical prolapse.

According to still further features in the described preferred embodiments the tissue repair device is a mesh, a sling or a suture.

According to still further features in the described preferred embodiments (c) is effected via a tissue anchor attached to the tissue repair device.

According to another aspect of the present invention there is provided a system for repairing a pelvic floor disorder comprising a housing for interconnecting: (a) an imaging device configured for positioning in or against a rectal, perianal or vaginal cavity; and (b) a surgical instrument for delivering a tissue repair device to a target tissue through a vaginal wall; wherein the housing includes a guide for aligning a path of the surgical instrument with an imaging field of the imaging device.

According to still further features in the described preferred embodiments the imaging device is an ultrasound transducer and the guide element aligns the path of the surgical instrument with an imaging plane of the ultrasound transducer.

According to still further features in the described preferred embodiments the target tissue is a sacrospinous ligament.

According to still further features in the described preferred embodiments the vaginal wall is a posterior vaginal wall.

According to still further features in the described preferred embodiments the pelvic floor disorder is central pelvic apical prolapse.

According to still further features in the described preferred embodiments the tissue repair device is a mesh, a sling or a suture.

According to still further features in the described preferred embodiments the surgical instrument is capable of anchoring the tissue repair device to the target tissue. According to still further features in the described preferred embodiments the anchoring is effected via a tissue anchor forming a part of the tissue repair device.

According to still further features in the described preferred embodiments the surgical instrument is configured with a tissue piercing end.

The present invention successfully addresses the shortcomings of the presently known configurations by providing a system that can be used to access pelvic floor tissues and guide a tissue repair device to an anatomical landmarks and structures through the access path.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1E illustrate one embodiment of the present system, showing the imaging device and holder in a disassembled (FIG. 1A), and assembled (FIG. 1B) states, showing loading of the surgical instrument and attached mesh (FIGS. 1C-1D) and showing a side view of the system with the angle between surgical instrument (A) and US holder and distance to target (L).

DESCRIPTION OF SPECIFIC EMBODIMENTS OF THE INVENTION

Figure 1A:
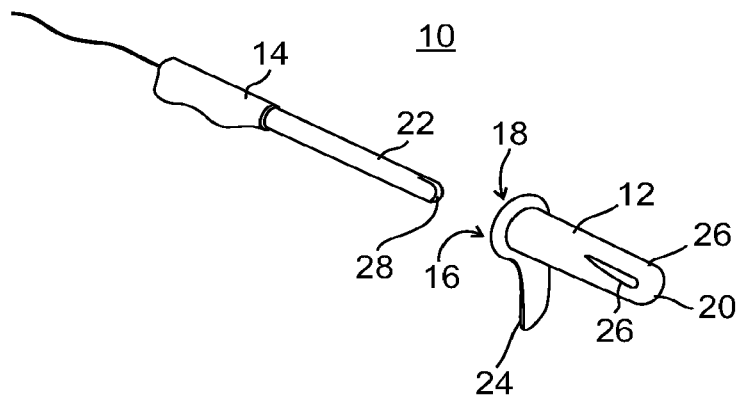

The present invention is of a system and method which can be used to provide access to anatomical landmarks as well as guide the positioning of tissue repair devices such as sutures, slings and/or meshes used to repair pelvic floor disorders.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description, Example or drawings. The invention is capable of other embodiments or of being practiced or carried out in various ways. Also, it is to be understood that the phraseology and terminology employed herein is for the purpose of description and should not be regarded as limiting.

Pelvic organ prolapse (POP), and especially apical central supportive defect (ACSD), significantly affects the quality of life of about 20% of the female population. POP is typically corrected via a transabdominal or a transvaginal surgical procedure.

The transvaginal reconstruction approach is regarded as superior to the transabdominal approach due to a shorter operative time and hospital stay and quicker rehabilitation. However, transvaginal procedures require advanced surgical skill and as such are performed by a rather small and highly qualified group of surgeons.

In the transvaginal procedure, a surgeon can elect to suspend the vaginal apex (VA) or the uterine cervix (UC) to the sacrospinous-ligament (SSL), sacrum, arcus tendineous fascia pelvis (ATFP) or other potentially solid supportive pelvic structures, which are accessed via anterior or posterior vaginal wall incisions and blunt dissection of tissues.

Creating an access path to these tissues is a major challenge of transvaginal procedures since it requires complicated navigation to the pelvic side wall (PSW), ischial spine (IS) and then to the mid SSL (MSSL) or the sacrum which carries with it a risk of damaging the bladder, rectum, blood vessels, nerves, ureters, etc.

Most POP procedure complications are attributed to the dissection necessary to create the tissue path to the elected tissue support site.

In order to traverse these limitations of prior art transvaginal procedures, the present inventors have devised an approach for directly and accurately accessing anatomical landmarks within the pelvic floor while minimizing tissue trauma and complications.

Thus, according to one aspect of the present invention there is provided a method of repairing a pelvic floor disorder.

As used herein, the phrase "pelvic floor disorder" refers to any disorder of the pelvic floor that is associated with prolapse, herniation or incorrect anatomical positioning of pelvic floor tissues.

The term "repair" when used herein with reference to pelvic floor disorders refers to correction (complete or incomplete) of anatomy, via, a tissue repair device such as a suture, a mesh, a sling and/or the like. An example of a repair procedure effected using the present methodology and system is described below.

Centro-apical reconstruction is key to proper pelvic organ prolapse (POP) repair. The premium supportive pelvic structure is the sacrospinous ligament (SSL), positioned at the posterior aspect of the pelvis. The SSL is high, thus provides a level 1 support by DeLancey. The SSL is a stable anatomical landmark and as such it is highly suitable for anchoring support.

The method of the present invention is effected by positioning an imaging device in or against an abdominal, rectal, anal or vaginal cavity and advancing a surgical instrument through a vaginal wall under guidance of the imaging device to thereby reach a target tissue within the pelvic floor (e.g. SSL). Once at the target tissue, the surgical instrument can be used to attach a tissue repair device (e.g. mesh) to the target tissue.

Imaging enables direct visualization of the MSSL and accurate navigation of the surgical instrument thereto providing a surgeon with transvaginal access to the MSSL through the lateral vaginal wall and minimizing risks associated with posterior or anterior access (injury to the rectum or bladder).

The imaging device and surgical instrument need not be physically interconnected during the procedure. However, as is further described hereinunder, use of a housing that interconnects the imaging device and surgical instrument and provides guides for aligning the surgical instrument with the imaging field of the imaging device provides several advantages and is presently preferred.

The imaging device can be any type of imaging device suitable for tissue imaging from within the rectal, or vaginal cavity or against the abdominal or anal cavity. Intravaginal or intra-rectal imaging device are preferred. Examples of suitable imaging devices include infrared imaging devices and the like. Such devices are configured so as to enable insertion into, and use within the cavity of choice.

One presently preferred imaging device is an ultrasound transducer. Ultrasound imaging from within the rectal, or vaginal cavity is well known in the art and commonly practiced. Gynecologists utilize trans-vaginal ultrasound (US) for amniocentesis and ovum retrieval or for in vitro fertilization (IVF). Urologists utilize trans-rectal US for prostate biopsies.

The surgical instrument can be any instrument capable of puncturing the vaginal wall and driving a repair device through the tissue and into the target site. One example of a surgical instrument includes an elongated shaft connected at a proximal end to a working handle. The shaft length can be anywhere from 3 to 15 cm with a diameter of 3-15 mm. The distal end of the shaft can be configured for tissue puncturing (beveled, double beveled or conical) and include an element (hook, harpoon, groove etc.) for holding and delivering a repair device (suture, mesh). The surgical instrument can also be configured for enlarging and maintaining open a tissue path created by the shaft. Such features of the surgical device can be provided by a toroidal inflatable balloon (positioned along the shaft length) or by outwardly expanding mechanical structures (e.g. wire meshes, struts and the like) that are capable of pushing the tissue around the shaft radially outward and holding the formed tissue channel open to allow deployment and fixation of a repair device.

The surgical instrument can also include a sensor (at the distal tip) for identifying proximity to the tissue site of interest and an imaging marker for identifying the tip of the shaft via the imaging device. An example of an echogenic marker is provided in US 20050228288.

The imaging device and surgical instrument can be used in a pelvic floor procedure by positioning the imaging device against an abdominal or anal cavity or preferably in a rectal, or vaginal cavity to provide imaging of the pelvic floor tissues of interest (target tissues as well as tissue on path that are to be avoided) and using the imaging field to guide a surgical instrument through the vaginal wall (e.g. posterior) and into pelvic floor tissues.

As is mentioned hereinabove, the present method if preferably effected an imaging device which interconnected to the surgical instrument via a housing.

Thus, according to one aspect of the present invention there is provided system for pelvic floor repair.

The housing of the present system can interconnect any imaging device (configured for placement in any of the cavities described herein) with the surgical instrument. The housing preferably provides a guide (track, rail, channel, groove etc.) which determines the path of insertion for the surgical instrument through the vaginal wall and underlying tissues. Such a path is preferably aligned with the imaging field of the imaging device.

In configurations of the present system which include an imaging device that is positioned in or against cavity displaced from the vaginal cavity (e.g. anal, rectal), the housing guide is configured to accommodate for such displacement and provide the correct path for the surgical instrument.

One preferred configuration of the present system which is referred to herein as system 10 is illustrated in FIGS. 1A-1E. System 10 utilizes an ultrasound imaging device which is configured for vaginal positioning.

Figure 1B:
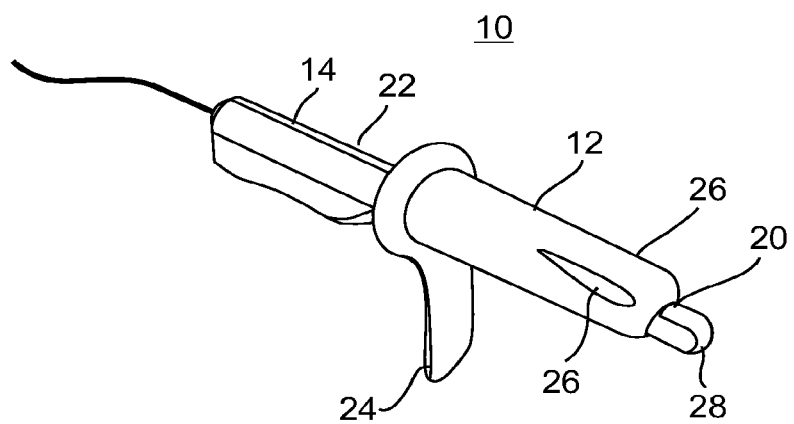

System 10 includes a housing 12 and an imaging device 14 (shown separately in FIG. 1A and assembled in FIG. 1B). Housing 12 can be fabricated from a polymer or alloy using molding or forming techniques. Since housing 12 is utilized within the vaginal cavity it is fabricated from a material that can be sterilized and possibly re-sterilized following use (although a disposable configuration of housing 12 is preferred).

Housing 12 is typically cylindrical in shape with a length of 5-10 cm and a diameter of 1-5 cm. Housing 12 includes a lumen 16 having a proximal opening 18 through which a transducer 22 is loaded and a distal opening 20 through which an imaging head 28 of transducer 22 protrudes. Lumen 16 is configured for accommodating an imaging transducer 22 and as such it is dimensioned for tightly fitting transducer 22. Lumen can also include elements (e.g. tabs) for releasably locking transducer 22 within lumen. Housing 12 further includes a handle 24 to enable maneuvering of the transducer 18-housing 12 assembly within the vaginal cavity.

Figure 1C:
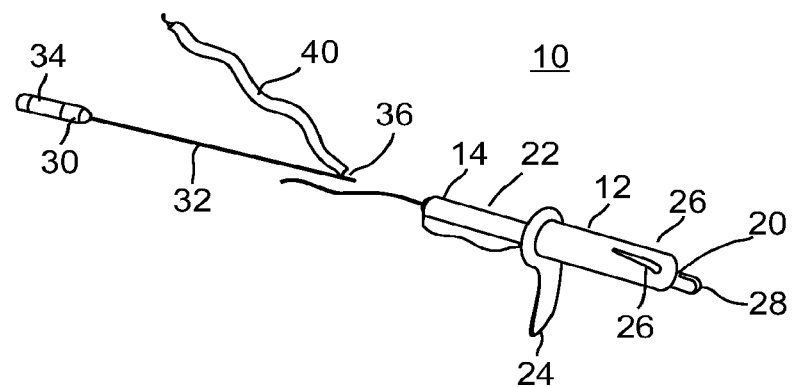
Figure 1D:
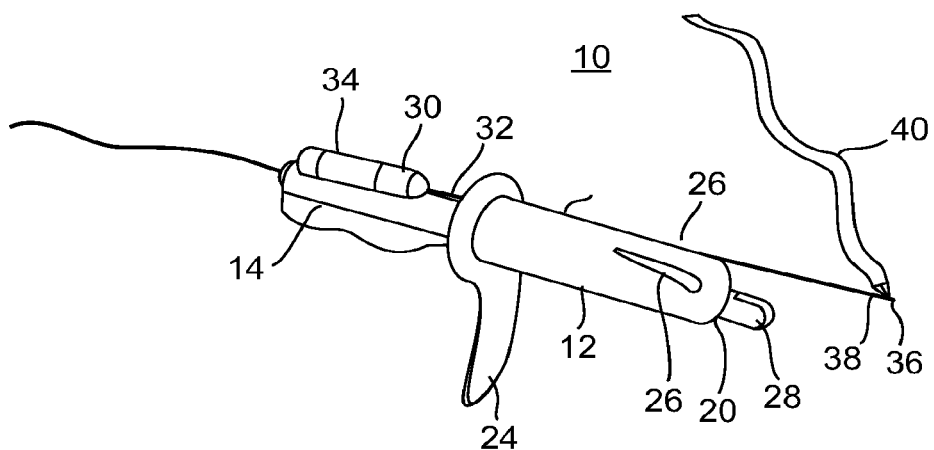

Housing 12 also includes at least one guide 26 (two shown) for guiding a surgical instrument 26 (shown in FIGS. 1C-1D). Guides 26 are configured as open channels or slots with an internal diameter of 3-10 mm and a length of 20-150 mm. Guides 16 can be slightly angled (outward) with respect to an imaging plane of imaging head 28. Two or more guides 26 provide optional paths for a surgical instrument 30 (FIGS. 1C-1D) depending on the positioning of housing 12 and transducer 18 with respect to the tissue.

Surgical instrument 30 includes an elongated shaft 32 which is connected at a proximal end thereof to a handle 34. A distal end portion 36 of shaft 32 is configured for tissue piercing and includes an element 38 for holding and delivering a tissue repair device 40 to a target tissue.

As is shown in FIG. 1E, when used for delivering a suture or mesh to the SSL (described in detail below), surgical instrument 30 is angled (A) with respect to housing 12 at about 15-35 degrees. In addition, surgical instrument 30 is configured having a length (about 20-40 cm) for enabling delivery of the tip of surgical instrument 30 through the vaginal wall tissue and into the SSL (a distance L, about 3.5 cm) by a user holding the proximal end of surgical instrument 30.

Figure 2A:
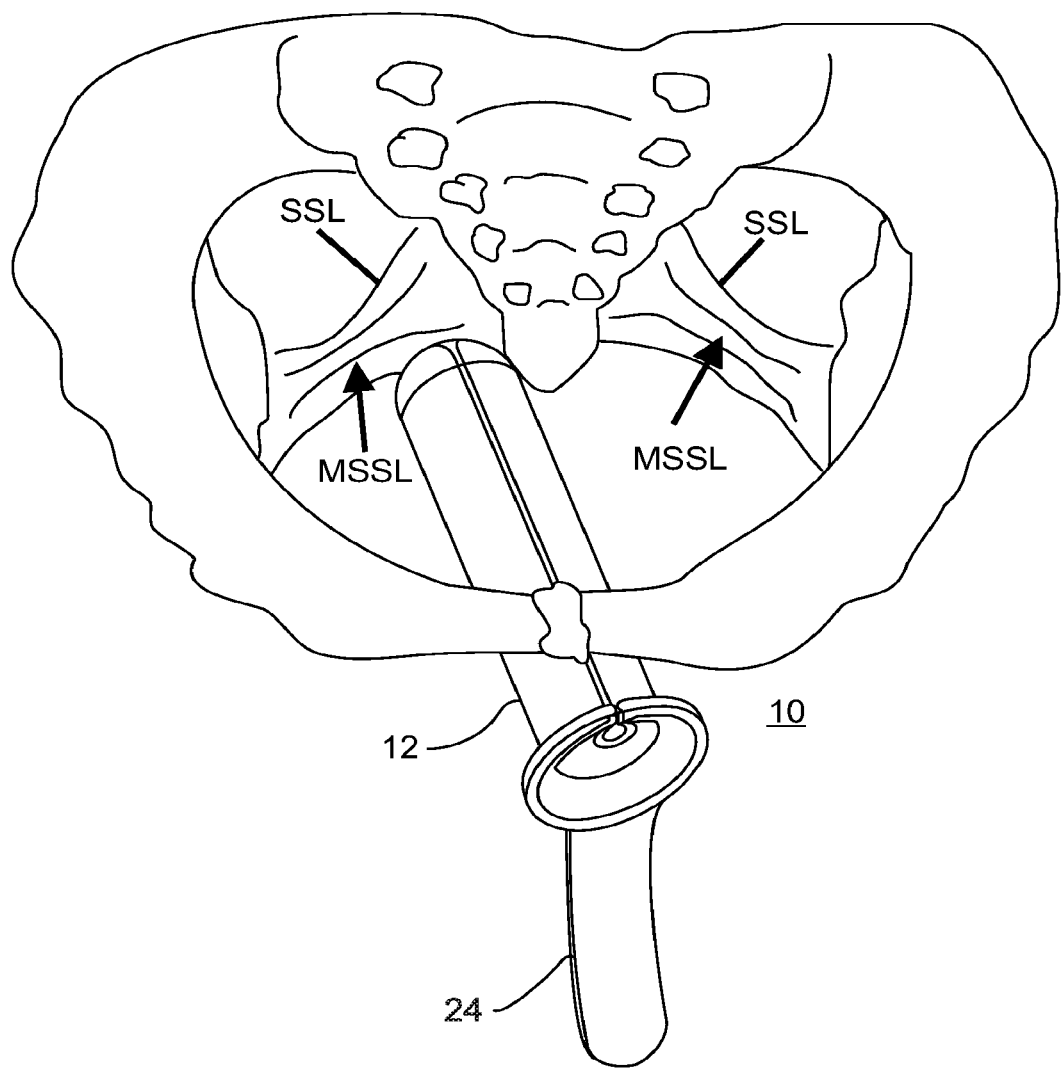
FIGS. 2A-2E illustrate a pelvic floor procedure using the system of FIGS. 1A-1D.
Figure 2B:
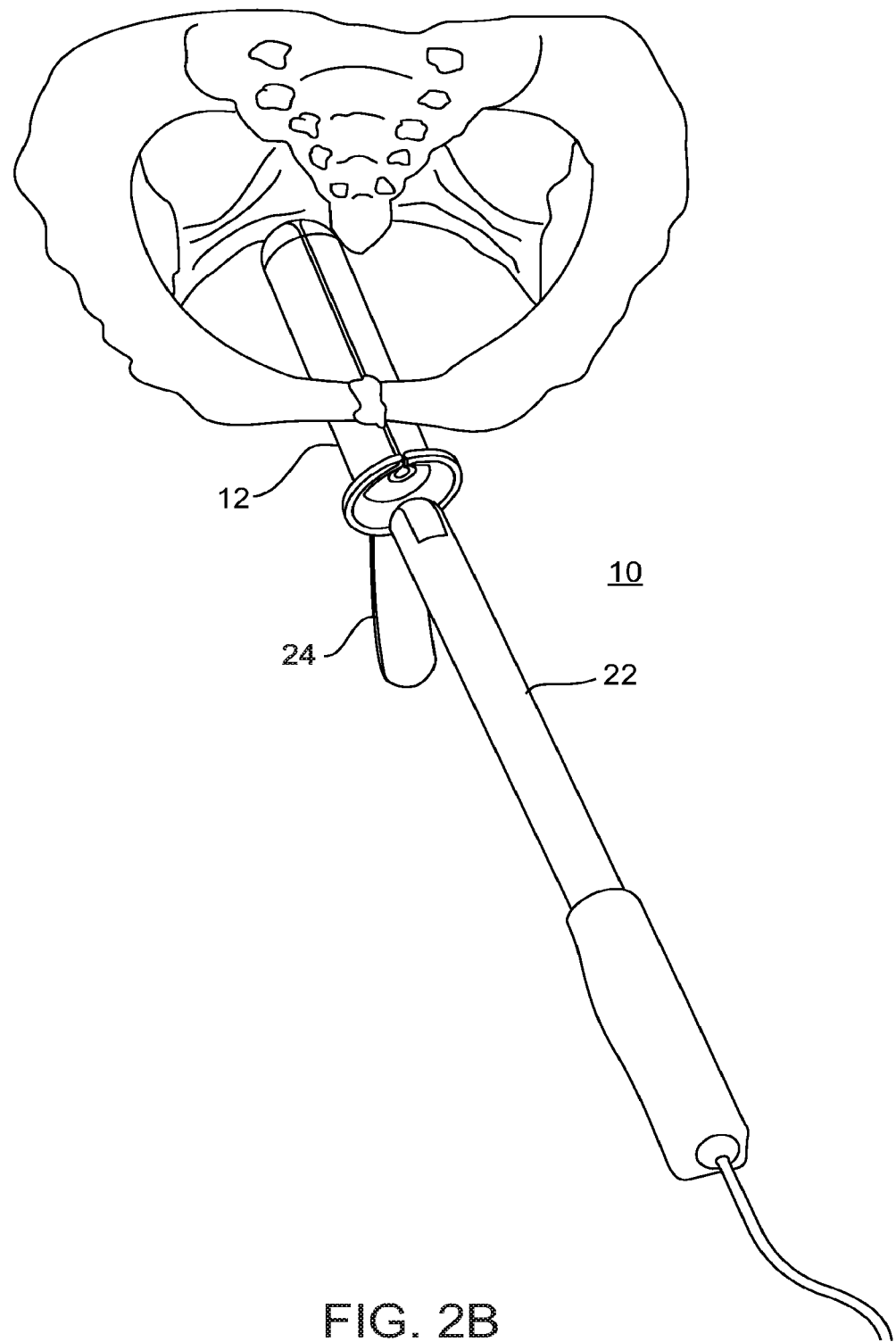
Figure 2C:
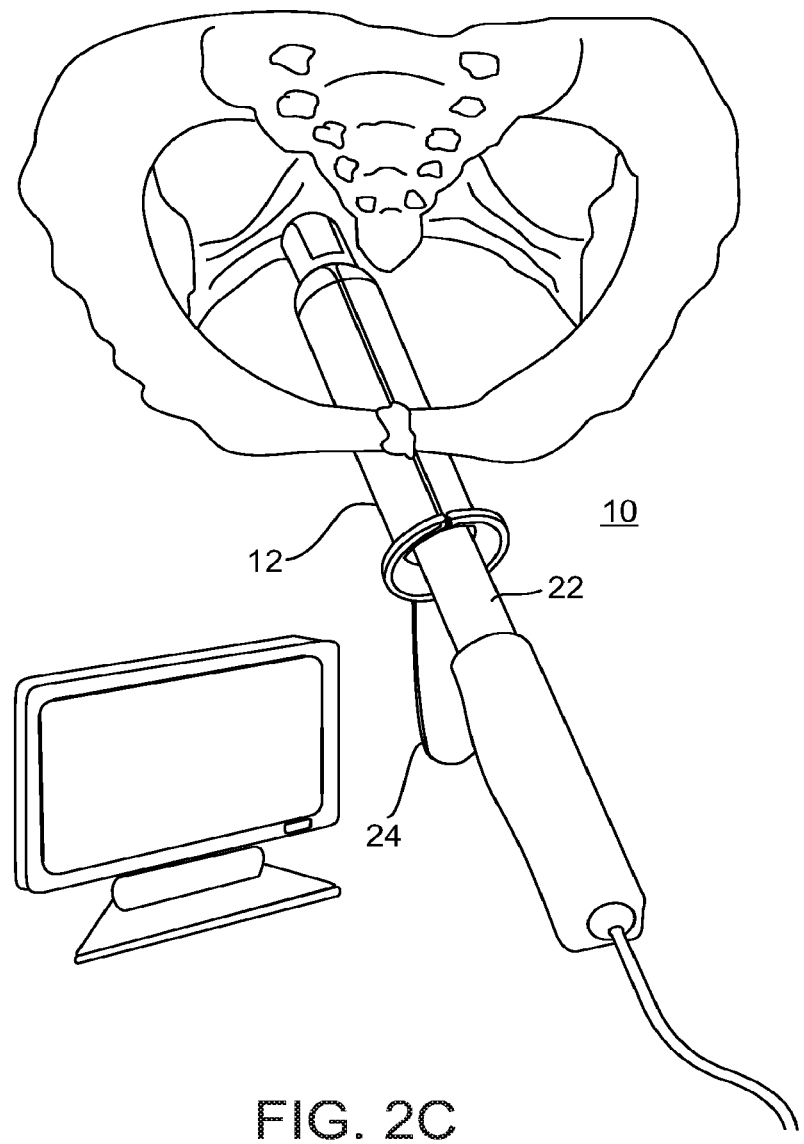
Figure 2D:
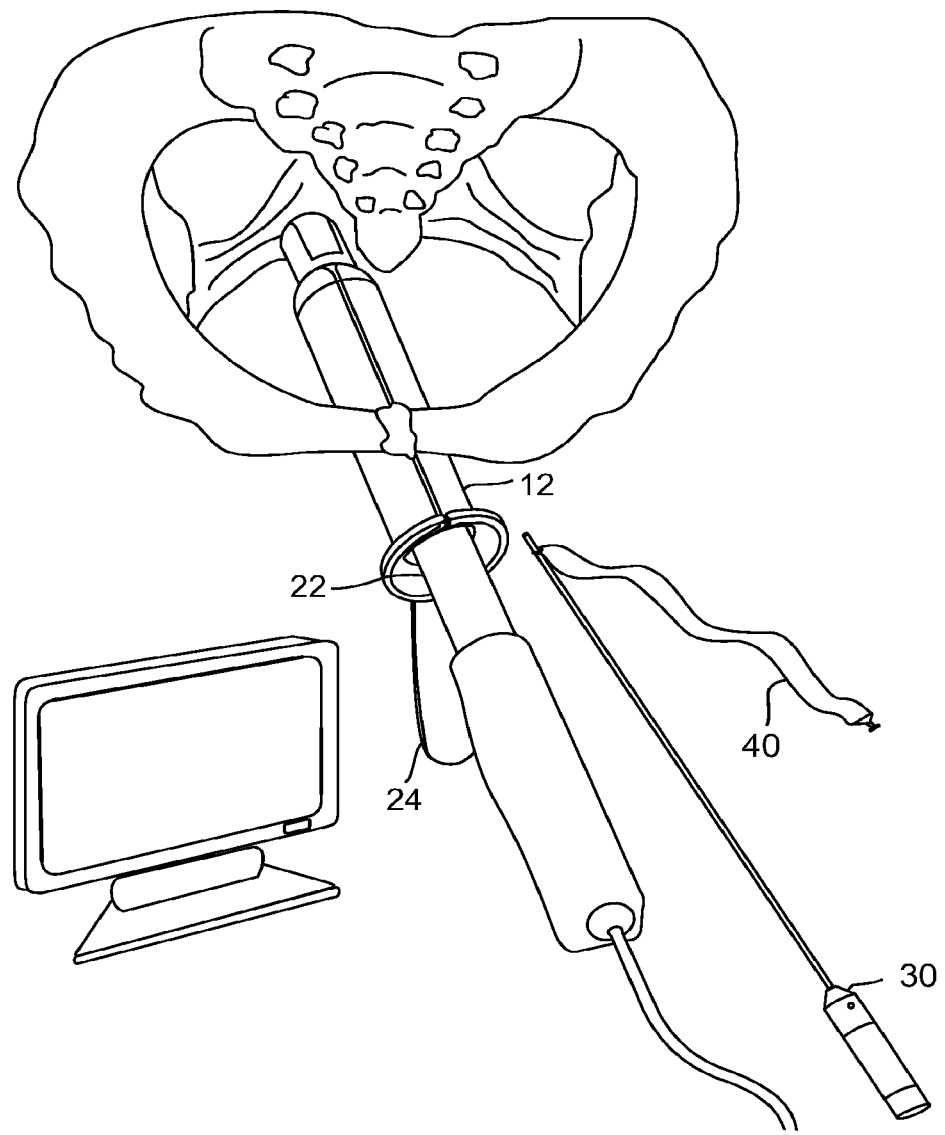

Surgical instrument 30 is loaded through guide 26 as shown in FIGS. 2C-2D and maneuvered using guide 26 to the target tissue. When utilized with an ultrasound transducer, the distance and angle between the longitudinal axis of guide 26 and the imaging plane of imaging head 28 is selected such that distal end portion 36 of instrument 30 advances within the imaging plane. This enables a user to track distal end portion 36 of surgical instrument 30 during delivery and ascertain the position thereof with respect to the target tissue while avoiding surrounding tissues such as the rectum etc.

Use of a system 10 which includes an ultrasound transducer and a housing configured for intravaginal imaging in a pelvic floor procedure is as follows. Housing 12 is inserted into the vaginal cavity (FIG. 2A) and imaging transducer 22 is loaded and locked within housing 12 (FIG. 2B-2C).

Figure 2E:
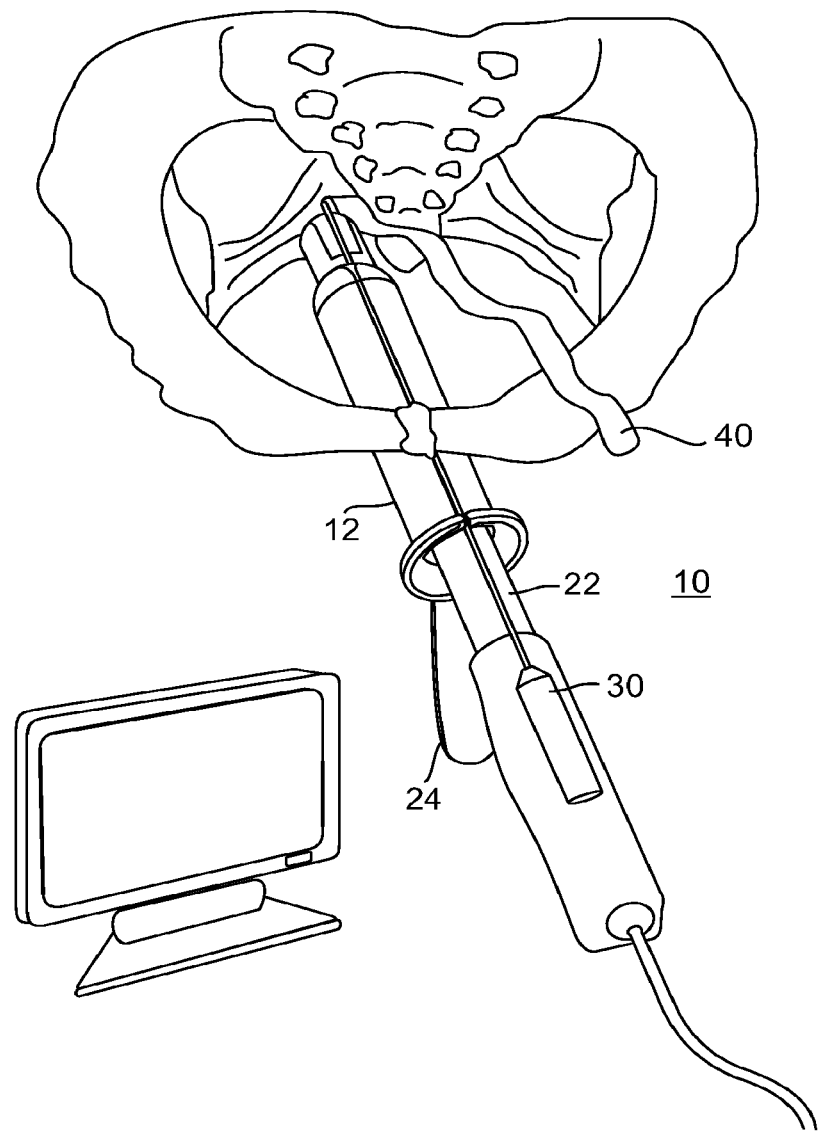

Handle 24 of housing 12 is used to insert imaging transducer 22 endovaginally in a frontal position at an angle of 40-60 degrees below "the horizon" (i.e. below the longitudinal axis of the vaginal canal) without applying pressure to the vaginal wall while imaging the rectum and levator ani muscles. Imaging transducer 22 is advanced deeper into the vagina towards the uterine cervix or vaginal apex, it is then rotated into a sagittal position and advanced into the direction of the ischial spine. Imaging head 28 of imaging transducer 22 is used to identify hyper-echogenic band structure corresponding to the SSL (see FIG. 2A) or the sacro-tuberous ligament (not shown) and the length of the SSL is measured. Doppler US is then used to identify vascular structures which in turn help to identify the location of the pudendal nerve. The MSSL (see FIG. 2A) is then identified and aligned with the imaging field of imaging transducer 22. Surgical instrument 30 (e.g. harpoon anchor) carrying a suture/mesh is loaded into guide 26 (FIG. 2D) and advanced through the vaginal wall at, for example, posterior or the lateral fornix (FIG. 2E) while imaging the SSL and the tip of surgical instrument 30 (which includes an echogenic marker). Surgical instrument 30 is pushed through the MSSL to anchor a suture/mesh carried thereby into the SSL. A suture/mesh can also be anchored to the mid-tubero sacral ligament (MTSL).

A uterine cervix connector coupled to the US transducer can be used to standardize the procedure and in particular the insertion of the surgical instrument through the vaginal apex. Such a connector can also facilitate fixation of the fibrotic ring of the uterine cervix to the MSSL-anchored repair device.

Surgical instrument 30 is then pulled out leaving a proximal end of the suture/mesh in the vagina. The procedure is repeated on the other side of the patient with a second suture/mesh, leaving 2 (or more—as much as the surgeon feels needed) suture/mesh ends in the vagina.

An incision of about 1 cm can be created in the vaginal wall between the 2 suture/mesh and the ends are tied or sutured to the apex of the vaginal vault or to the cervix (for uterine prolapse reconstruction). Alternatively, the uterine cervix fixation might be achieved with an anchoring device, glue or any other supportive technique.

The actual distance between imaging head 28 and the target tissue (e.g. MSSL) can be around 2 cm. As such, surgical instrument 30 loaded into guide 26 can easily be pushed through the tissue to deliver a repair device (e.g. a harpoon anchor attached to suture/mesh etc.) to the MSSL under US-Doppler imaging, thus avoiding the damage to unwanted structures in the area (e.g. blood vessels).

System 10 of the present invention can be used with any transvaginal pelvic floor repair procedure and in any patients suffering from a pelvic floor disorder which is characterized by weak soft tissues at the vaginal apex resulting in urological, gynecological, and gastroenterological anatomical changes.

The present approach can be supplemented with cervical fixation via suture to the uterine cervix or, if the patient has undergone hysterectomy, to the vaginal apical sub-mucosal or any other vaginal tissue or to the remnants of the sacro-uterine ligaments. Such a suture can be delivered through the vaginal mucosa or through a vaginal posterior or anterior incision. The cervical and SS or ST ligament fixating sutures can then be attached to each other with a knot tying device or a suture or clip or anchor etc.

Fixation tension can that needs to be adjusted to a tension free level, by suture tying or a ratchet mechanism (positioned at the retro-vaginal space) can be used to adjust tension at any point desired by the surgeon following the procedure.

Thus, the present invention provides a system and method which can be used to perform transvaginal pelvic floor procedures. The present invention is advantageous in that:

(i) it does not require posterior or anterior vaginal dissections which can jeopardize the rectum or bladder;

(ii) it enables direct visualization of the target tissue (e.g. MSSL) for accurate navigation of a minimally invasive surgical instrument;

(iii) US provides a clear image of the surgical instrument tip at the MSSL, since the region of convergence at the US image midline between the surgical instrument tip and the MSSL is small (0.5-2.0 cm in length);

(iv) It minimizes unwanted damage to visceral and vessel tissue during the procedure; and (v) it eliminates the need for deep pelvic manual dissection and Hydrodis section.

Table 1 below summarizes the advantages of the present invention over presently used techniques.

TABLE 1

| Approach | Anterior or Posterior | lateral vaginal wall |
| --- | --- | --- |
| Blunt dissection | Large | Minimal dissection |
| Distance to SSL | 9 cm | 2.5 cm |
| Visualization | Blind | Ultrasound |
| Safety | Might perforate rectum, bladder | No risk for perforation |
| Access to SSL | Long and potentially harmful path | Short and Safe |
| Bleeding | Vessels and arteries can't be seen, potential for bleeding is high | Visualize with US Doppler to avoid vessels and arteries |
| Pudendal nerve injury risk | High | Very low |

By minimizing bleeding and perforation risks the present invention could be used to bridge the gap between the advanced surgical skills required for performing present POP reconstruction procedures and the average surgeon skills. This could render colposacropexy (CSP), colposacrospinopexy (CSSP), hysterosacropexy (HSP) and hysterosacrospinopexy (HSSP) an office procedure with minimal risk and short recovery times.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Ultrasound Imaging of the Ischial Spines and Sacrospinous Ligaments

The anatomy of the pelvic floor of women suffering from POP was imaged using ultrasound in order to find out if ultrasound imaging can be used to identify the SSL and Ischial Spine. Doppler imaging was also used to identify blood vessels at the area of the SSL.

Figure 3:
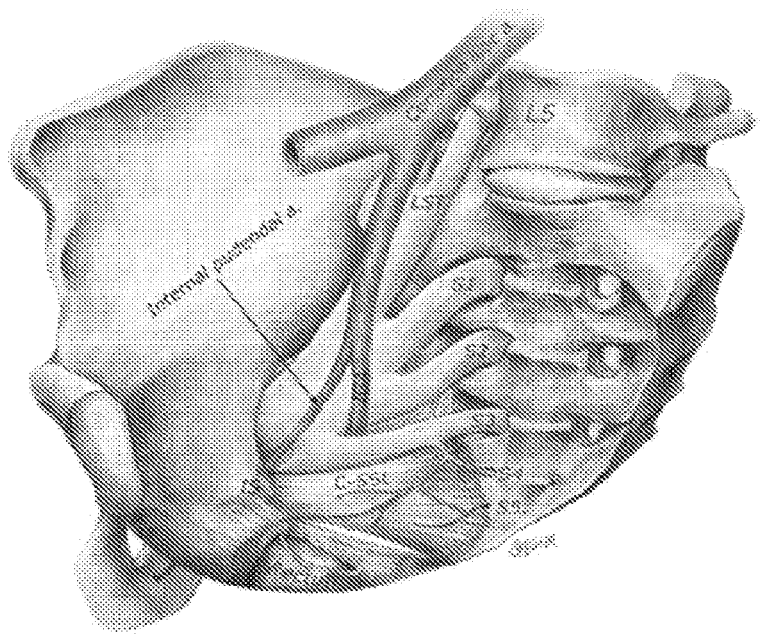
FIG. 3 is a prior art image of the posterior pelvic floor.
Figure 4A:
FIGS. 4A-4F are intravaginal ultrasound images of the pelvic floor showing the SSL and IS.
Figure 4B:
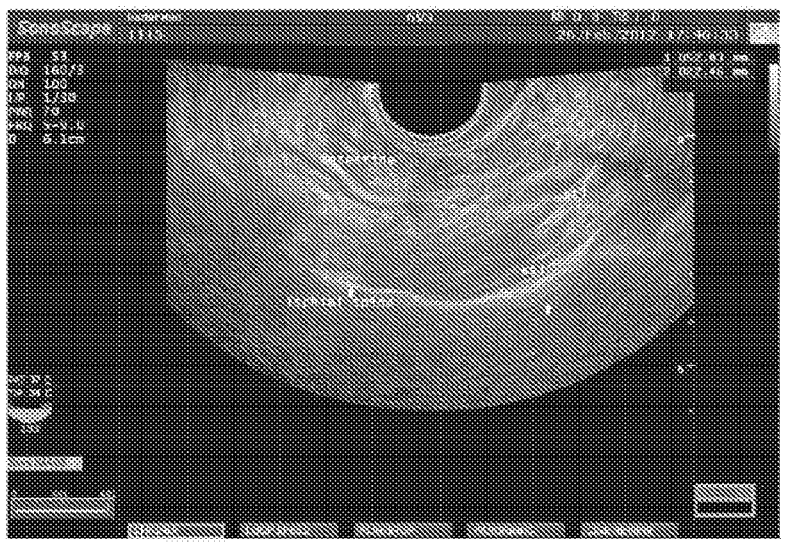
Figure 4C:
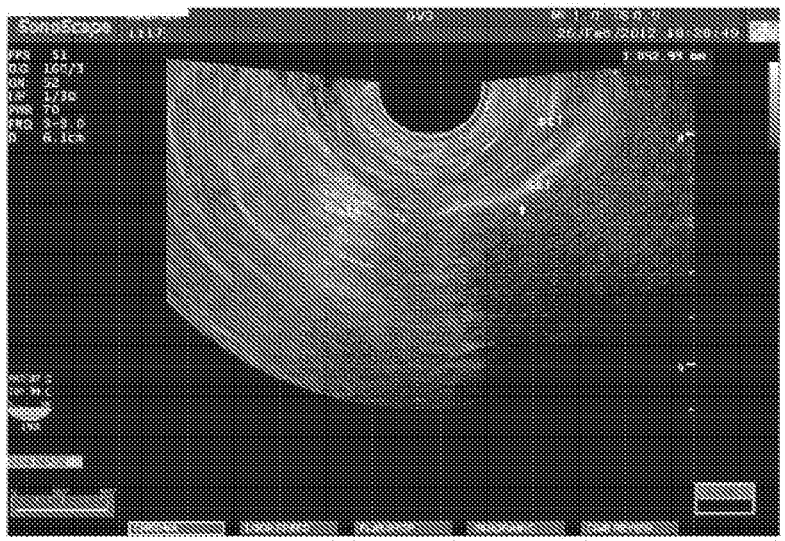
Figure 4D:
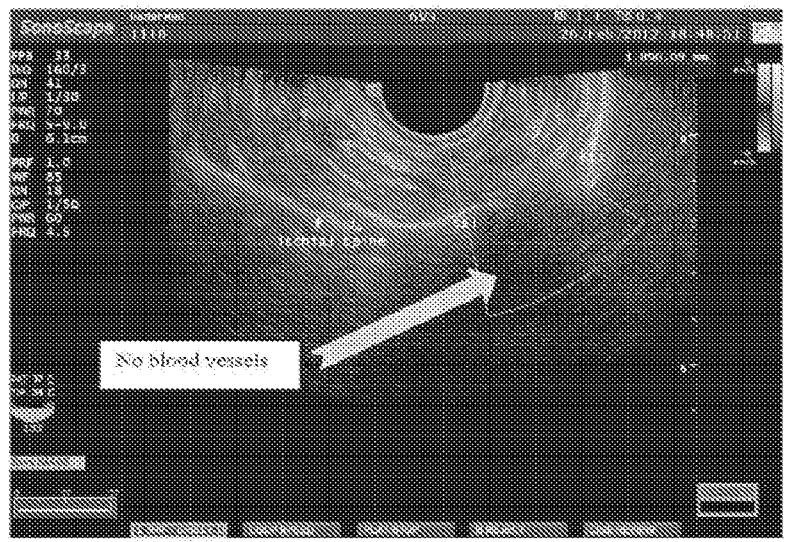
Figure 4E:
Figure 4F:
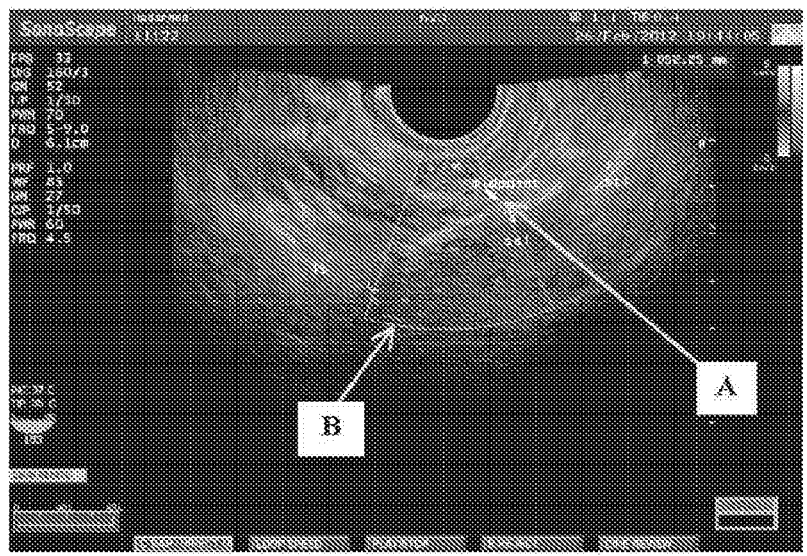

As is shown in FIG. 3, the SSL includes dense connective tissue and contributes to the stability of the bony pelvis. It attaches to the ischial spine laterally and lower part of the sacrum and coccyx medially. The sacrospinous, along with the sacrotuberous ligament, divides the sciatic notches of the ischium into the lesser and greater sciatic foramen (GSF). The internal pudendal and inferior gluteal vessels, sciatic nerve, and other branches of the sacral nerve plexus pass through the GSF in close proximity to the ischial spines and SSL.

On the superior or pelvic surface of the SSL lies the coccygeus muscle, which together with the levator ani muscles comprises the pelvic diaphragm. The coccygeus muscle has the same bony attachments and runs an identical course to the SSL; thus, many refer to these structures as the coccygeus-SSL (C-SSL) complex. The average length of the right C-SSL complex is 53.7 mm and that of the left C-SSL is 53.6 mm.

Methods

Two dimensional (2D) intravaginal ultrasound (US) was performed on 10 female subjects diagnosed with POP using the SonoScape S8 portable Ultrasound. The SSL and IS were identified in all 10 subjects.

The US transducer was inserted in the frontal position with no pressure on vaginal wall (visualizing rectum and levator ani muscles). The transducer was then advanced deeper into the vagina towards the uterine cervix or vaginal apex and rotated into a sagittal position while being advanced towards the ischial spine. Hyper echogenic bands representing the SSL and the sacro-tuberous ligament were identified and the length of the SSL was measured. Vascular structures were identified using Doppler ultrasound; the position of these vascular structures helped to determine the location of the pudendal nerve.

Results

FIGS. 4A-4F are US images captured during the procedure. The US images were captured using an end-fire probe which enabled the identification of the ischial spine and SSL, Doppler imaging enabled identification of blood vessels.

The SSL and IS landmarks were identified in all ten subjects tested. Measurements of SSL were taken in all 10 subjects and were at the average described above. Vascular structures surrounding the SSL were identified and were used to locate the pudendal nerve running behind the SSL thus providing additional safety measures for preventing damage to the nerve during a POP procedure. In conclusion, the present study conclusively showed that ultrasound imaging can provide a safe 'straight-shot' delivery path to the midpoint of the SSL.

Example 2

Cadaver Study

A cadaver study was undertaken in order to identify and measure the distance and path between anatomical landmarks within the posterior pelvis and the vaginal apex.

Materials and Methods

Figure 5A:
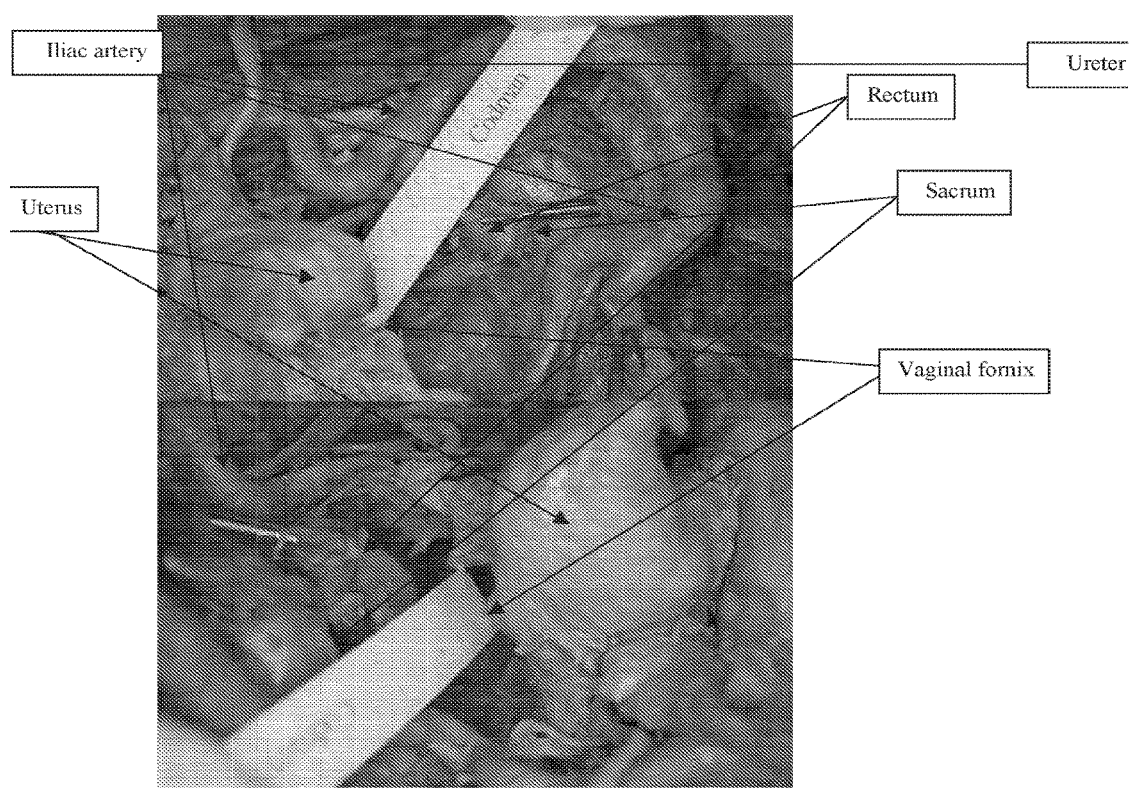
FIGS. 5A-5B illustrate the anatomical landmarks identified in the cadaver study.
Figure 5B:
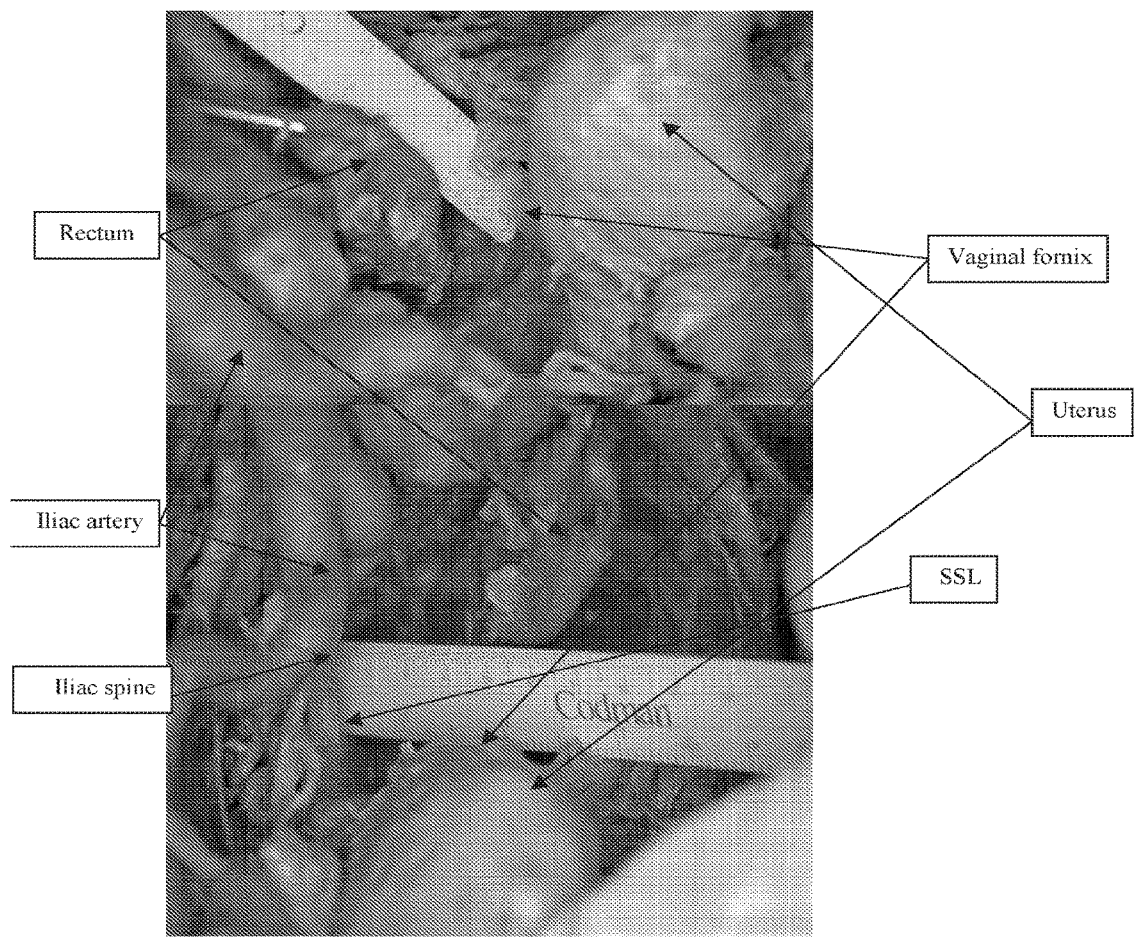

An abdominal dissection was performed on a formalin-embedded human cadaver while in a dorso-supine position. The vaginal apex was identified and marked and an ultrasound probe was inserted into the vaginal canal. Anatomical landmarks within the posterior pelvis including the MSSL, the MSTL, the ischial spine, the sacrum, the rectum, the pudendal bundle and the iliac vessel were identified and their distance from the apex was measured using a ruler (FIGS. 5A-5B).

Results

The results are presented in Table 2 below.

TABLE 2

| Anatomical landmark | Distance from US probe tip (in cm) | comments |
|---|---|---|
| MSSL | 3.5 | |
| MSTL | 4.5 | angled 45-60 downwards |
| Ischial spine | 4.5 | |
| Sacrum | 3.5 | |
| Rectum | 2.5 | |
| Pudendal bundle | 4.5 | |
| Iliac vessels | 5.5 | |

Conclusions

The vaginal capacity and elasticity were limited due to the fact that a non-POP formalin embedded cadaver was utilized in this study. Thus, the above listed posterior pelvic landmarks could not be palpated upon vaginal examination thereby necessitating anatomical dissection.

The above listed anatomical structures were clearly identified following dissection; measurements of distances between these structures and the vaginal fornix enabled identification of a safe needle path from the vaginal fornix to the MSSL or MSTL.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for attaching an anchor to a ligament located outside of a tissue wall, the system comprising:
   a body-insertable mounting having a longitudinal axis;
   a working channel extending at an angle with respect to said longitudinal axis, mounted onto said body-insertable mounting; and
   a suture and penetrating anchor assembly which is configured to be axially displaceable along said working channel through said tissue wall and into anchoring relationship with said ligament, said suture and penetrating anchor assembly including a proximity sensor at a distal end thereof.

2. A system according to claim 1 and wherein said suture and penetrating anchor assembly comprises a laterally expandable anchor.

3. A system according to claim 1 and wherein said suture and penetrating anchor assembly is configured to remain at said angle with respect to said longitudinal axis when displaced through said tissue wall into said anchoring relationship with said ligament.

\* \* \* \* \*